(12) United States Patent
White

(10) Patent No.: US 12,042,391 B2
(45) Date of Patent: Jul. 23, 2024

(54) ORTHOPAEDIC IMPLANT SYSTEM WITH HINGE

(71) Applicant: DePuy Synthes Products, Inc., Raynham, MA (US)

(72) Inventor: Stephen E. White, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1120 days.

(21) Appl. No.: 16/863,156

(22) Filed: Apr. 30, 2020

(65) Prior Publication Data

US 2020/0352727 A1    Nov. 12, 2020

Related U.S. Application Data

(60) Provisional application No. 62/844,929, filed on May 8, 2019.

(51) Int. Cl.
*A61F 2/38* (2006.01)

(52) U.S. Cl.
CPC ............ *A61F 2/385* (2013.01); *A61F 2/3859* (2013.01); *A61F 2/389* (2013.01); *A61F 2002/3863* (2013.01)

(58) Field of Classification Search
CPC . A61F 2/3859; A61F 2/385; A61F 2002/3863
See application file for complete search history.

(56) References Cited

U.S. PATENT DOCUMENTS

| | | | |
|---|---|---|---|
| 3,748,662 | A | 7/1973 | Helfet |
| 5,219,362 | A | 6/1993 | Tuke et al. |
| 5,370,701 | A | 12/1994 | Finn |
| 5,682,886 | A | 11/1997 | Delp et al. |

(Continued)

FOREIGN PATENT DOCUMENTS

| | | |
|---|---|---|
| EP | 1604623 A1 | 12/2005 |
| EP | 2572677 A1 | 3/2013 |

(Continued)

OTHER PUBLICATIONS

PCT International Search Report for International Application No. PCT/IB20/54110, dated Aug. 12, 2020; 3 pages.

(Continued)

*Primary Examiner* — Jason-Dennis N Stewart
(74) *Attorney, Agent, or Firm* — Barnes & Thornburg LLP

(57) ABSTRACT

An orthopaedic prosthesis includes a tibial tray, a tibial insert configured to be coupled to the tibial tray, a hinge component configured to be received in a passageway of the tibial tray, and a femoral component configured to articular with the tibial insert. The hinge component includes a pair of hinge arms, each of which includes an axle extending therefrom that is configured to be received in an aperture of a corresponding sidewall of an intercondylar compartment of the femoral component. The axles of the hinge arms may be coaxial or non-coaxial. Additionally, each axle may be coaxial with or offset from a center of a constant radius of curvature that defines an articular surface of a corresponding condyle of the femoral component. The axles may have an outer surface of various shapes depending on the embodiment.

19 Claims, 13 Drawing Sheets

(56) References Cited

U.S. PATENT DOCUMENTS

| | | | |
|---|---|---|---|
| 5,735,856 | A | 4/1998 | Mccue et al. |
| 5,871,018 | A | 2/1999 | Delp et al. |
| 5,964,808 | A | 10/1999 | Blaha et al. |
| 6,013,103 | A | 1/2000 | Kaufman et al. |
| 6,986,791 | B1 | 1/2006 | Metzger |
| 7,261,740 | B2 | 8/2007 | Tuttle et al. |
| 8,187,335 | B2 | 5/2012 | Wyss et al. |
| 8,192,498 | B2 | 6/2012 | Wagner et al. |
| 8,211,181 | B2 | 7/2012 | Walker |
| 8,236,061 | B2 | 8/2012 | Heldreth et al. |
| 8,292,964 | B2 | 10/2012 | Walker |
| 8,328,873 | B2 | 12/2012 | Metzger et al. |
| 8,480,752 | B2 | 7/2013 | Dun |
| 8,628,579 | B2 | 1/2014 | Ries et al. |
| 8,784,496 | B2 | 7/2014 | Wagner et al. |
| 8,795,380 | B2 | 8/2014 | Heldreth et al. |
| 8,828,086 | B2 | 9/2014 | Williams et al. |
| 8,834,575 | B2 | 9/2014 | Wyss et al. |
| 8,915,965 | B2 | 12/2014 | Komistek |
| 9,101,393 | B2 | 8/2015 | Jordan et al. |
| 9,101,394 | B2 | 8/2015 | Arata et al. |
| 9,168,145 | B2 | 10/2015 | Wyss et al. |
| 9,216,088 | B2 | 12/2015 | Wasielewski |
| 9,220,601 | B2 | 12/2015 | Williams et al. |
| 9,299,138 | B2 | 3/2016 | Zellner et al. |
| 9,320,616 | B2 | 4/2016 | Samuelson et al. |
| 9,320,624 | B2 | 4/2016 | Shin |
| 9,326,864 | B2 | 5/2016 | Wyss et al. |
| 9,402,726 | B2 | 8/2016 | Linderman et al. |
| 9,452,053 | B2 | 9/2016 | Wagner et al. |
| 9,539,099 | B2 | 1/2017 | Heldreth et al. |
| 9,603,711 | B2 | 3/2017 | Bojarski et al. |
| 9,668,870 | B2 | 6/2017 | Wasielewski |
| 9,788,954 | B2 | 10/2017 | Parisi et al. |
| 9,820,821 | B2 | 11/2017 | Aram et al. |
| 9,861,446 | B2 | 1/2018 | Lang |
| 9,931,216 | B2 | 4/2018 | Williams et al. |
| 9,937,049 | B2 | 4/2018 | Wyss et al. |
| 9,962,264 | B2 | 5/2018 | Komistek |
| 10,080,663 | B2 | 9/2018 | Wasielewski |
| 10,159,530 | B2 | 12/2018 | Lang |
| 10,179,051 | B2 | 1/2019 | Heldreth et al. |
| 10,179,052 | B2 | 1/2019 | Clary et al. |
| 10,195,056 | B2 | 2/2019 | Wogoman et al. |
| 10,201,429 | B2 | 2/2019 | Enomoto et al. |
| 10,265,180 | B2 | 4/2019 | Wyss et al. |
| 10,278,827 | B2 | 5/2019 | Drury et al. |
| 10,478,307 | B2 | 11/2019 | Wasielewski et al. |
| 10,543,098 | B2 | 1/2020 | Williams et al. |
| 10,729,551 | B2 | 8/2020 | Heldreth et al. |
| 10,849,760 | B2 | 12/2020 | Wyss et al. |
| 11,141,291 | B2 | 10/2021 | Wogoman et al. |
| 11,229,485 | B2 | 1/2022 | Otto et al. |
| 11,324,598 | B2 | 5/2022 | Dai et al. |
| 11,337,823 | B2 | 5/2022 | Williams et al. |
| 11,364,081 | B2 | 6/2022 | Dees, Jr. |
| 11,369,478 | B2 | 6/2022 | Wyss et al. |
| 11,612,488 | B2 | 3/2023 | Wogoman et al. |
| 2003/0009228 | A1 | 1/2003 | Figueroa et al. |
| 2005/0107886 | A1 | 5/2005 | Crabtree et al. |
| 2005/0278035 | A1 | 12/2005 | Wyss et al. |
| 2008/0262812 | A1 | 10/2008 | Arata et al. |
| 2008/0269596 | A1 | 10/2008 | Revie et al. |
| 2009/0088860 | A1 | 4/2009 | Romeis et al. |
| 2009/0204221 | A1 | 8/2009 | Walker |
| 2010/0036499 | A1 | 2/2010 | Pinskerova |
| 2010/0286788 | A1 | 11/2010 | Komistek |
| 2012/0197409 | A1 | 8/2012 | Mckinnon et al. |
| 2012/0265496 | A1 | 10/2012 | Mahfouz |
| 2012/0310246 | A1 | 12/2012 | Belcher et al. |
| 2012/0310362 | A1 | 12/2012 | Li et al. |
| 2013/0006373 | A1 | 1/2013 | Wyss et al. |
| 2013/0197653 | A1 | 8/2013 | Hawkins et al. |
| 2013/0197654 | A1 | 8/2013 | Samuelson et al. |
| 2013/0325021 | A1 | 12/2013 | Sordelet et al. |
| 2014/0039635 | A1 | 2/2014 | Bartels et al. |
| 2014/0081412 | A1 | 3/2014 | Metzger |
| 2014/0277534 | A1 | 9/2014 | Wasielewski |
| 2014/0330388 | A1 | 11/2014 | Mizuguchi et al. |
| 2015/0032215 | A1 | 1/2015 | Slamin et al. |
| 2015/0088264 | A1 | 3/2015 | Li et al. |
| 2015/0190235 | A1 | 7/2015 | Mcminn |
| 2016/0030184 | A1* | 2/2016 | Whiteside ............... A61F 2/385 |
| | | | 623/20.24 |
| 2016/0317312 | A1 | 11/2016 | Bojarski et al. |
| 2017/0020674 | A1 | 1/2017 | Walker |
| 2017/0079801 | A1 | 3/2017 | Drury et al. |
| 2017/0128219 | A1 | 5/2017 | Metzger et al. |
| 2017/0189191 | A1 | 7/2017 | Heldreth et al. |
| 2017/0189195 | A1 | 7/2017 | Blaha |
| 2017/0266013 | A1 | 9/2017 | Enomoto et al. |
| 2017/0340389 | A1 | 11/2017 | Otto et al. |
| 2019/0209331 | A1 | 7/2019 | Varadarajan et al. |
| 2019/0209333 | A1 | 7/2019 | Drury et al. |
| 2019/0240032 | A1 | 8/2019 | Wasielewski et al. |
| 2020/0069432 | A1 | 3/2020 | Mcminn |
| 2020/0085583 | A1 | 3/2020 | Hodge |
| 2020/0100902 | A1 | 4/2020 | Wasielewski et al. |
| 2020/0214843 | A1 | 7/2020 | Radermacher et al. |
| 2020/0246149 | A1* | 8/2020 | Matyas ................. A61F 2/3868 |
| 2022/0079678 | A1 | 3/2022 | Duxbury et al. |

FOREIGN PATENT DOCUMENTS

| | | |
|---|---|---|
| EP | 3854353 A1 | 7/2021 |
| WO | 9723172 A2 | 7/1997 |
| WO | 2010151564 A1 | 12/2010 |
| WO | 2011075697 A2 | 6/2011 |
| WO | 2014143538 A1 | 9/2014 |
| WO | 2017155995 A1 | 9/2017 |
| WO | 2017160889 A1 | 9/2017 |
| WO | 2017204832 A1 | 11/2017 |

OTHER PUBLICATIONS

Advance, Medial-Pivot and Stemmed Medial-Pivot Knee Systems, Wright Medical Technology, Inc., 2010, 12 pages.

Persona, The Personalized Knee, Surgical Technique, Zimmer Biomet, 2018, 76 pages.

Persona, The Personalized Knee, Medial Congruent Bearing Design Rationale, Zimmer Biomet, 2017, 20 pages.

eMP, Evolution, Medial-Pivot Knee System, The ACL-PCL Substituting Knee, Key Aspects, MicroPort Orthopaedics, 2015, 6 pages.

Evolution, Medial-Pivot Knee System, Surgical Technique, Distal Cut First, MicroPort Orthopaedics, 2014, 52 pages.

PCT Search Report & Written Opinion prepared for PCT/EP2021/069244, mailed Nov. 1, 2022, 24 pages.

Smith & Nephew, Journey II TKA Total Knee System—Combined Technique for Journey II BCS and Journey II CR, 68 pages.

International SR and Written Opinion for International App. No. PCT/US2020/022123, Completed May 8, 2020, 13 Pages.

International SR and Written Opinon for International App. No. PCT/US2020/022119, Completed May 27, 2020, 11 Pages.

International SR for International App. No. PCT/IB20/54105, Aug. 31, 2020, 3 Pages.

PCT International SR and Written Opinion for International App. No. PCT/EP2020/075246, Mar. 15, 2022, 11 Pages.

\* cited by examiner

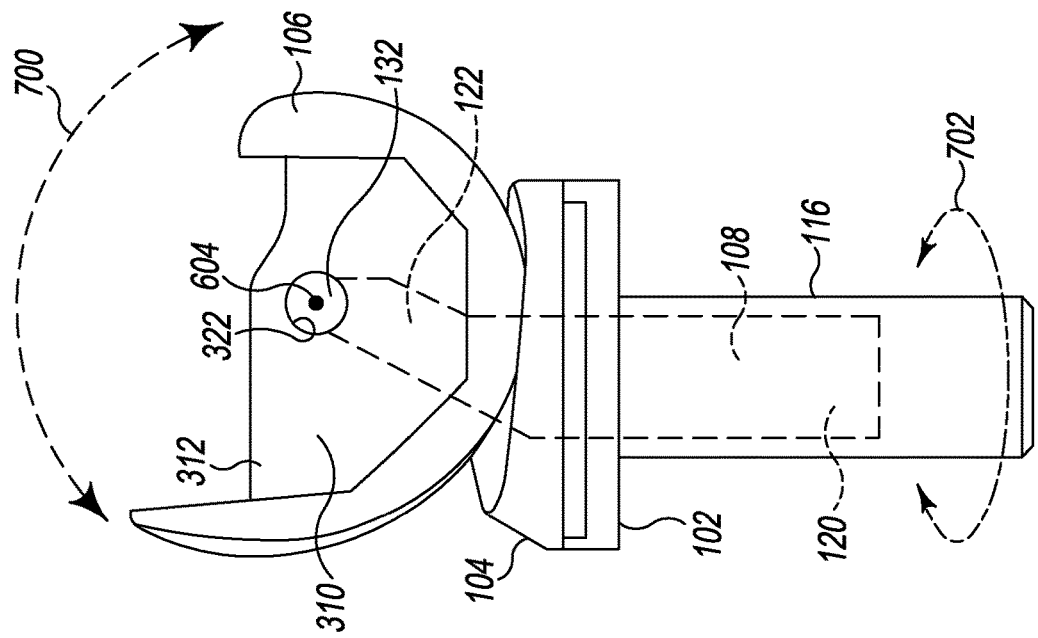
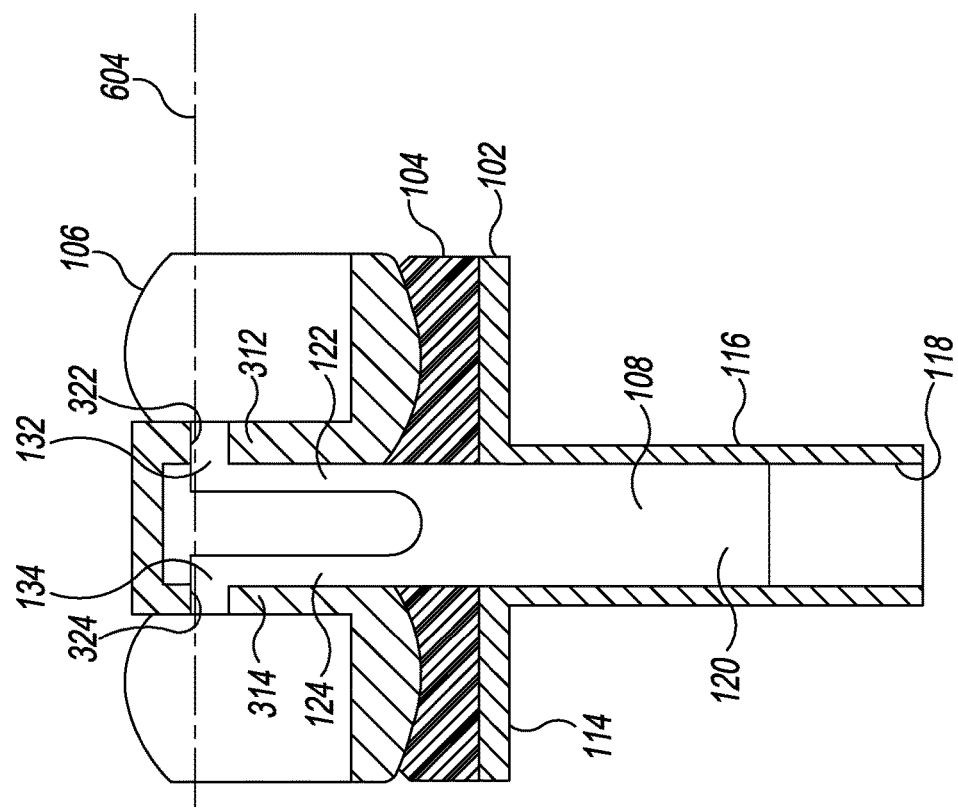
Fig. 7
Fig. 6

ORTHOPAEDIC IMPLANT SYSTEM WITH HINGE

CROSS-REFERENCE TO RELATED APPLICATIONS

The present patent application claims priority to and the benefit of U.S. Provisional Patent Application Ser. No. 62/844,929 entitled "ORTHOPAEDIC IMPLANT SYSTEM WITH HINGE," which was filed on May 8, 2019 and which is expressly incorporated by reference in its entirety into this application.

TECHNICAL FIELD

The present invention relates to orthopaedic prostheses, and, more particularly, to constrained orthopaedic prostheses.

BACKGROUND

Joint arthroplasty is a well-known surgical procedure by which a diseased and/or damaged natural joint is replaced by a prosthetic joint. A typical knee orthopaedic prosthesis includes a tibial tray, a femoral component, and a polymer insert or bearing positioned between the tibial tray and the femoral component. Depending on the severity of the damage to the patient's joint, knee orthopaedic prostheses of varying mobility may be used. For example, the knee orthopaedic prosthesis may include a "mobile" tibial insert in cases wherein a greater degree of freedom of movement is desired. Alternatively, the knee orthopaedic prosthesis may include a "fixed" tibial insert in cases wherein it is desirable to limit the movement of the knee orthopaedic prosthesis, such as when significant soft tissue damage or loss is present. In cases involving severe soft tissue damage or bone loss, a constrained orthopaedic knee prosthesis may be used. Constrained orthopaedic prostheses generally limit the mobility of the prosthetic joint to a single direction (e.g., rotation only in the anterior-posterior direction with not medial-lateral rotation). A hinged orthopaedic knee prosthesis is one type of a constrained orthopaedic prosthesis.

SUMMARY

According to an aspect of the present disclosure, an orthopaedic prosthesis includes a tibial tray, a tibial insert configured to be coupled to the tibial tray, a hinge component configured to be received in a passageway of the tibial tray, and a femoral component configured to articulate with the tibial insert. The tibial tray includes a platform configured to be coupled to a surgically-prepared surface of the proximal end of a tibia and a stem extending inferiorly from a bottom surface of the platform. The stem includes a longitudinal internal passageway. The tibial insert includes a pair of articular surfaces and an aperture defined between the pair of articular surfaces. The hinge component includes an elongated shaft configured to be received through the aperture of the tibial insert and into the longitudinal internal passageway of the tibial tray and a pair of hinge arms extending superiorly from a superior end of the elongated shaft. Each hinge arm includes an axle extending therefrom. The femoral component is configured to be coupled to a surgically-prepared surface of the distal end of a femur and includes a pair of spaced apart condyles configured to articulate on the articular surfaces of the tibial insert and an intercondylar compartment defined between the pair of spaced apart condyles. The intercondylar compartment includes a pair of side walls and each side wall includes an aperture. The axle of one of the hinge arms is configured to be received in the aperture of one of the side walls of the intercondylar compartment, and the axle of the other one of the hinge arms is configured to be received in the aperture of the other one of the side walls of the intercondylar compartment.

In some embodiments, the pair of hinge arms are moveable toward each other to allow insertion of the pair of hinge arms into the intercondylar compartment of the femoral component. Additionally, in some embodiments, the pair of hinge arms may include a medial hinge arm having a medial axle extending medially therefrom and a lateral hinge arm having a lateral axle extending laterally therefrom. In such embodiments, the pair of side walls may include a medial side wall having an aperture defined therein and a lateral side wall having an aperture defined therein. Additionally, in such embodiments, the medial axle of the medial hinge arm is configured to be received in the aperture of the medial side wall, and the lateral axle of the lateral hinge arm is configured to be received in the aperture of the lateral side wall. In some embodiments, each of the medial axle and the lateral axle is cylindrical.

In some embodiments, the medial axle and the lateral axle are coaxial with each other and cooperate to define a rotation axis about which the femoral component is configured to rotate in an anterior-posterior direction during articulation on the articular surfaces of the tibial insert. In such embodiments, the tibial insert may be configured to rotate on the platform in a medial-lateral direction about an axis defined by the stem of the platform. In some embodiments, the pair of spaced apart condyles of the femoral component includes a medial condyle having a medial articular surface defined by a first constant radius of curvature and a lateral condyle having a lateral articular surface defined by a second constant radius of curvature. In such embodiments, the rotation axis defined by the medial axle and the lateral axle may be coaxial with the center of the first constant radius of curvature and with the center of the second constant radius of curvature.

Additionally, in some embodiments, the pair of spaced apart condyles of the femoral component includes a medial condyle having a medial articular surface defined by a first constant radius of curvature and a lateral condyle having a lateral articular surface defined by a second constant radius of curvature. The center of the first constant radius of curvature may be coaxial with a center of the second constant radius of curvature to define a curvature axis. Additionally, the rotation axis defined by the medial axle and the lateral axle may be posteriorly offset from the curvature axis to cause posterior movement of the femoral component, relative to the tibial insert, during flexion of the orthopaedic prosthesis. For example, the rotation axis defined by the medial axle and the lateral axle may be posteriorly offset from the curvature axis by a distance of five to seven millimeters.

In some embodiments, the medial side wall of the intercondylar compartment may include a first aperture configured to receive the medial axle of the medial hinge arm and a second aperture configured to receive the medial axle and posteriorly offset from the first aperture. In such embodiments, the lateral side wall of the intercondylar compartment may include a first aperture configured to receive the lateral axle of the lateral hinge arm and located coaxially with the first aperture of the medial side wall and a second aperture configured to receive the lateral axle and located coaxially with the second aperture of the medial side wall.

Additionally, in some embodiments, the medial axle and the lateral axle are non-coaxial with each other. In such embodiments, the elongated shaft of the hinge component may include a medial elongated shaft component and a lateral elongated shaft component separate from the medial elongated shaft component. The medial hinge arm may extend superiorly from a superior end of the medial shaft component and the lateral hinge arm may extend superiorly from the lateral shaft component. Additionally, the medial axle may define a first axis and the lateral axle may define a second axis that is non-coaxial with the first axis.

In some embodiments, the pair of spaced apart condyles of the femoral component may include a medial condyle having a medial articular surface defined by a first constant radius of curvature and a lateral condyle having a lateral articular surface defined by a second constant radius of curvature. The first axis defined by the medial axle may be coaxial with a center of the first constant radius of curvature, and the second axis defined by the lateral axle may be posteriorly offset from a center of the second constant radius of curvature to cause posterior movement of the lateral condyle of the femoral component, relative to the medial condyle, during flexion of the orthopaedic prosthesis. For example, the second axis defined by the lateral axle may be posteriorly offset from the center of the second constant radius of curvature by five to seven millimeters.

Additionally, in some embodiments, the medial axle may have a hemispherical outer surface and the lateral axle have a hemispherical outer surface having a diameter that is less than a diameter of the hemispherical outer surface of the medial axle. In such embodiments, the aperture of the lateral side wall of the intercondylar compartment of the femoral component may have a diameter less than a diameter of the aperture of the medial side wall of the intercondylar compartment. Additionally, in such embodiments, the aperture of the medial wall may be configured to move posteriorly on the hemispherical outer surface of the medial axle and the aperture of the lateral wall may be configured to move anteriorly on the hemispherical outer surface of the lateral axle during flexion of the orthopaedic prosthesis.

According to another aspect, an orthopaedic prosthesis includes a tibial tray, a tibial insert, a hinge component, and a femoral. The tibial tray includes a platform configured to be coupled to a surgically-prepared surface of the proximal end of a tibia and a stem extending inferiorly from a bottom surface of the platform. The stem may include a longitudinal internal passageway. The tibial insert may be configured to be coupled to the platform and includes a medial articular surface, a lateral articular surface, and an aperture defined between the medial articular surface and the lateral articular surface. The hinge component includes an elongated shaft configured to be received through the aperture of the tibial insert and into the longitudinal internal passageway of the tibial tray. The elongated shaft includes a medial elongated shaft component and a lateral elongated shaft component separate from the medial elongated shaft component, a medial hinge arm extending superiorly from a superior end of the medial elongated shaft component and having a medial axle extending medially therefrom, wherein the medial axle has a hemispherical outer surface, and a lateral hinge arm extending superiorly from a superior end of the lateral elongated shaft component and having a lateral axle extending laterally therefrom. The lateral axle may have a hemispherical outer surface having a diameter that is less than a diameter of the hemispherical outer surface of the medial axle and wherein the medial axle and the lateral axle are non-coaxial. The femoral component is configured to be coupled to a surgically-prepared surface of the distal end of a femur and includes a medial condyle configured to articulate on the medial articular surface of the tibial insert, a lateral condyle configured to articulate on the lateral articular surface of the tibial insert, and an intercondylar compartment defined between the pair of spaced apart condyles. The intercondylar compartment may include a medial side wall having an aperture defined therein and a lateral side wall having an aperture defined therein that has a diameter less than a diameter of the aperture defined in the medial side wall. The medial axle may be configured to be received in the aperture of the medial side wall and the lateral axle may be configured to be received in the aperture of the lateral side wall.

In some embodiments, the medial condyle of the femoral component may include a medial articular surface defined by a first constant radius of curvature and the lateral condyle may include a lateral articular surface defined by a second constant radius of curvature. In such embodiments, the first axis defined by the medial axle may be coaxial with a center of the first constant radius of curvature, and the second axis defined by the lateral axle may be posteriorly offset from a center of the second constant radius of curvature to cause posterior movement of the lateral condyle of the femoral component, relative to the medial condyle, during flexion of the orthopaedic prosthesis.

According to a further aspect, a hinge component for a hinged orthopaedic prosthesis may include an elongated shaft, a medial hinge, and a lateral hinge. The elongated shaft may be configured to be received into an internal passageway of a tibial tray. The medial hinge may extend superiorly from the elongated shaft and may include a medial axle extending medially therefrom. The lateral hinge arm may extend superiorly from the elongated shaft and may include a lateral axle extending laterally therefrom. The medial hinge arm and the lateral hinge arm may be movable toward each other to allow insertion of the medial and lateral arms into an intercondylar compartment of a femoral component.

In some embodiments, the elongated shaft may include a medial elongated shaft component and a lateral elongated shaft component separate from the medial elongated shaft component. In such embodiments, the medial hinge arm extends superiorly from a superior end of the medial shaft component and the lateral hinge arm extends superiorly from the lateral shaft component. The medial axle defines a first axis and the lateral axle defines a second axis that may be coaxial or non-coaxial with the first axis.

BRIEF DESCRIPTION OF THE DRAWINGS

The detailed description particularly refers to the following figures, in which:

FIG. 6 is an anterior cross-sectional elevation view of the orthopaedic knee prosthesis of FIG. 1 in the assembled configuration;

FIG. 7 is a medial elevation view of the orthopaedic knee prosthesis of FIG. 1 in the assembled configuration and showing the hinge component in phantom;

DETAILED DESCRIPTION OF THE DRAWINGS

Figure 1:
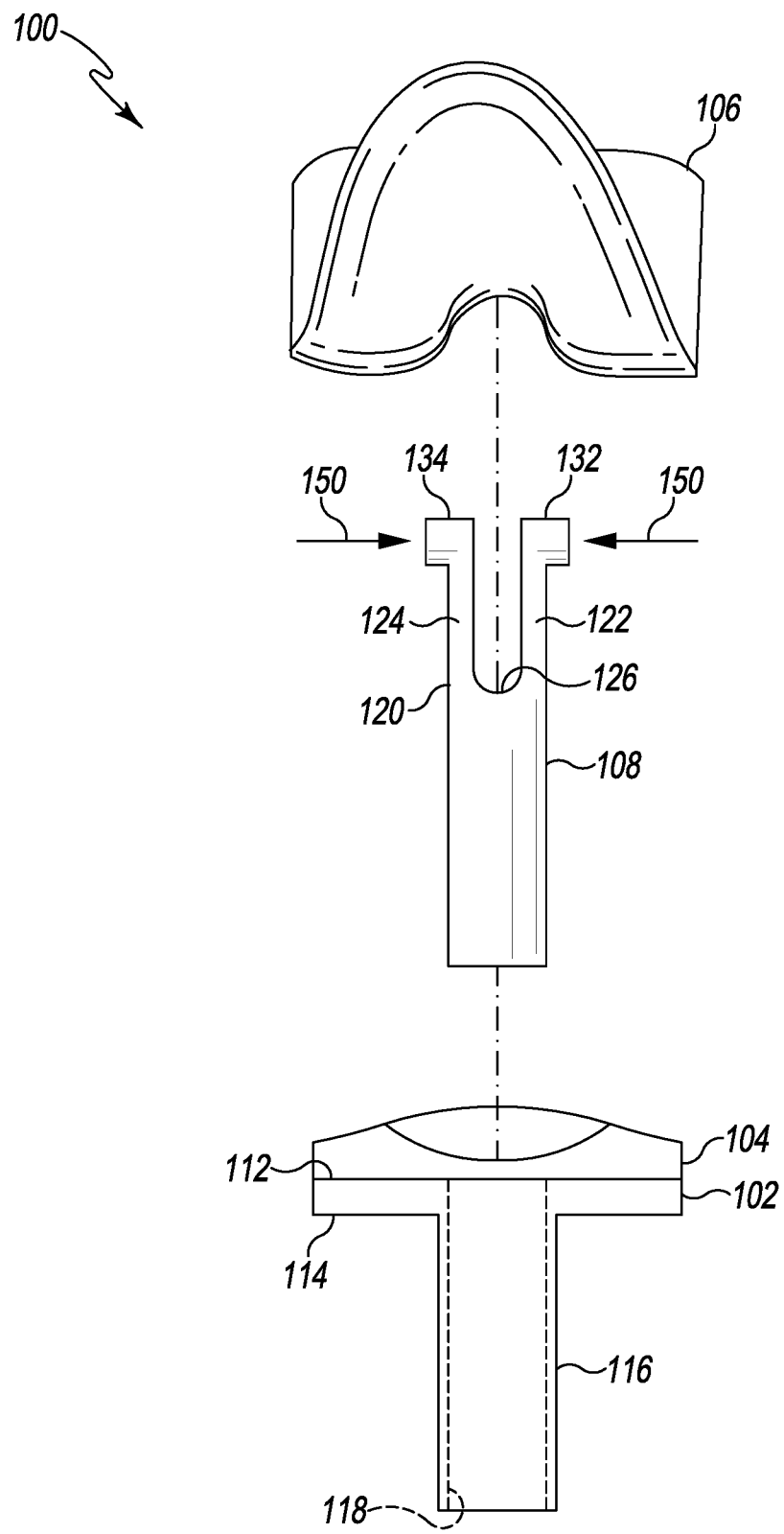
FIG. 1 is a partially-exploded elevation view of an embodiment of an orthopaedic knee prosthesis including a femoral component, a hinge component, a tibial insert, and a tibial tray.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. While the disclosure below describes techniques and instrument system in reference to a patient's tibia, it should be appreciated that all of the systems and techniques described below may be used to surgically prepare other bones, such as, for example, a distal end of a patient's femur.

Referring now to FIG. 1, an illustrative orthopaedic knee prosthesis 100 includes a tibial tray 102, a tibial insert 104 configured to mount on the tibial tray 102, a femoral component 106 configured to articulate with the tibial insert 104, and a hinge component 108 configured to be received in the tibial tray 102 and connected to the femoral component 106 to control rotational motion of the femoral component 106 as discussed in more detail below. The tibial tray 102 and the femoral component 106 are illustratively formed from a metallic material, such as cobalt-chromium or titanium. The tibial insert 104 and the hinge component 108 are illustratively formed from a polymer material such as an ultra-high molecular weight polyethylene (UHMWPE). Of course, any of the tibial tray 102, tibial insert 104, femoral component 106, and/or hinge component 108 may be formed from other materials, such as a ceramic material, a polymer material, a metallic material, a bio-engineered material, or other implantation-grade material, in other embodiments.

The illustrative tibial tray 102 is configured to be coupled to a surgically-prepared surface of the proximal end of a tibia of a patient. The tibial tray 102 includes a platform 110 having a superior or upper surface 112 and an inferior or bottom surface 114. The tibial tray 102 also includes a stem 116 that extends inferiorly or downwardly from the inferior surface 114. The stem 116 includes a longitudinal internal passageway 118 defined therein. The longitudinal internal passageway 118 may be embodied as a blind or non-blind passageway. When the tibial tray 102 is implanted in the patient's tibia, the bottom surface 114 of the platform 110 abuts or confronts the surgically-prepared surface of the patient's tibia and the stem 116 is received in a surgically-prepared medullary canal of the patient's tibia.

Figure 2:
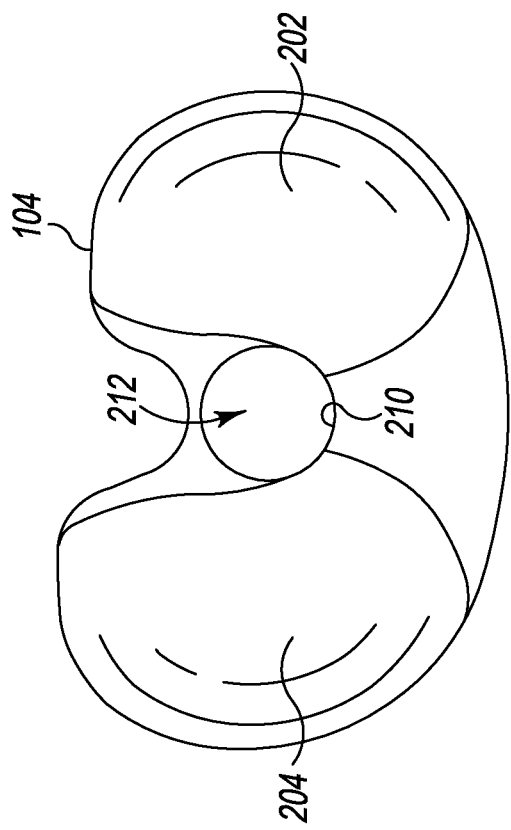
FIG. 2 is a plan view of an embodiment of the tibial insert of the orthopaedic prosthesis of FIG. 1.
Figure 5:
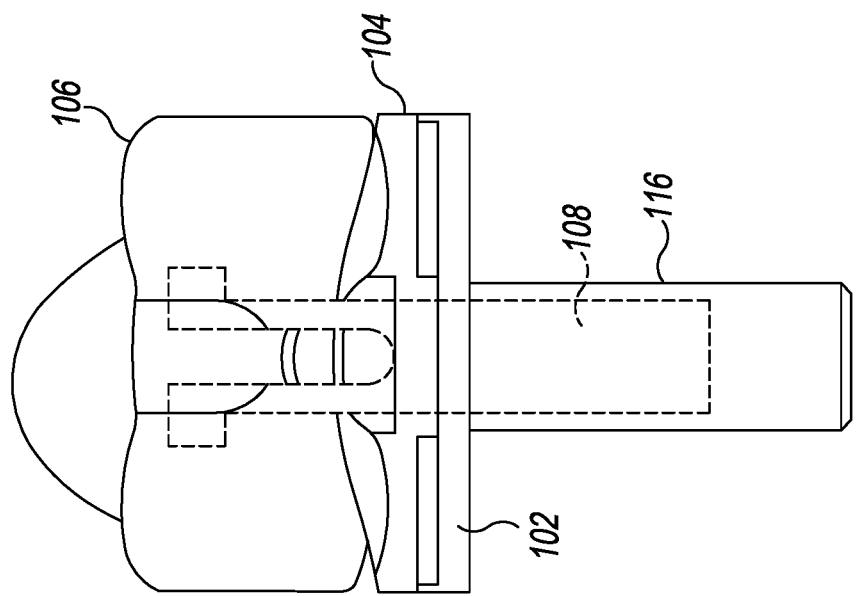
FIG. 5 is an posterior elevation view of the orthopaedic knee prosthesis of FIG. 1 in the assembled configuration and showing the hinge component in phantom.
Figure 4:
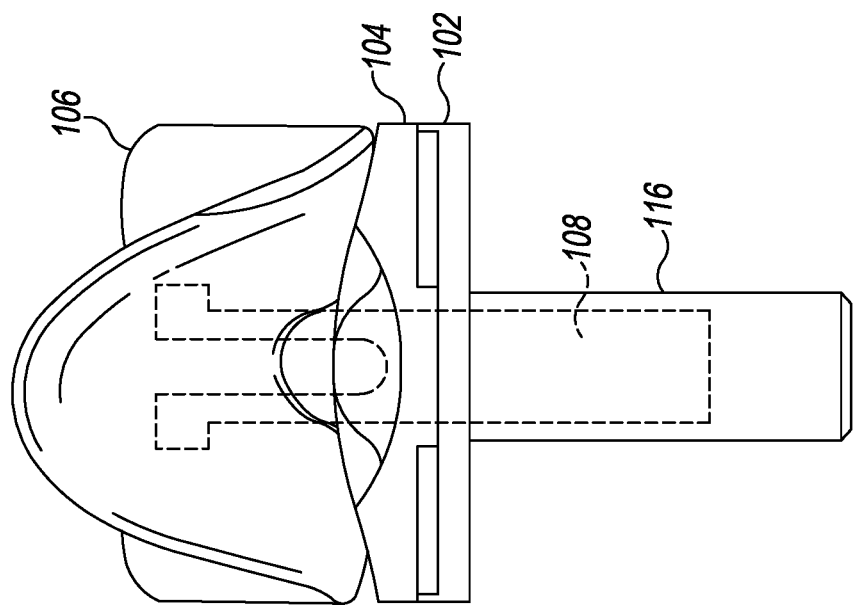
FIG. 4 is an anterior elevation view of the orthopaedic knee prosthesis of FIG. 1 in an assembled configuration and showing the hinge component in phantom.

As best shown in FIG. 2, the illustrative tibial insert 104 includes a medial articular surface 202 and a lateral articular surface 204. The articular surfaces 202, 204 are illustratively asymmetrically shaped to provide asymmetric pivoting of the femoral component 106 when articulating on the tibial insert 104 as discussed in more detail below. That is, the articular surface 202 is shaped differently from the articular surface 204. For example, in the illustrative embodiment, the medial articular surface 202 is more conforming to the medial condyle of the femoral component 106 than the lateral articular surface 204 is to the lateral condyle of the femoral component 106. As such, the lateral articular surface 204 may be larger than the medial articular surface 202. Of course, in other embodiments, the articular surfaces 202, 204 may be symmetrically-shaped.

The tibial insert 104 also includes an inner wall 210 that defines an aperture 212 through the tibial insert 104. The aperture 212 is shaped and sized to allow the hinge component 108 to be inserted therethrough and into the longitudinal internal passageway 118 of the stem 116 of the tibial tray 102 when the orthopaedic knee prosthesis 100 is assembled as discussed below. Illustratively, the aperture 212 has a circular shape but may have other shapes and dimensions in other embodiments based on, for example, the shape of the hinge component 108.

The tibial insert 104 is illustratively embodied as a "fixed" tibial insert in which the tibial insert 104 is secured to the tibial tray 102 in such a manner that medial-lateral rotation of the tibial insert 104 is restricted or prevented. However, in other embodiments, the tibial insert 104 may be embodied as a "mobile" or rotating tibial insert configured to rotate in a medial-lateral direction about an axis defined by the stem 116 of the tibial tray 102.

Figure 3:
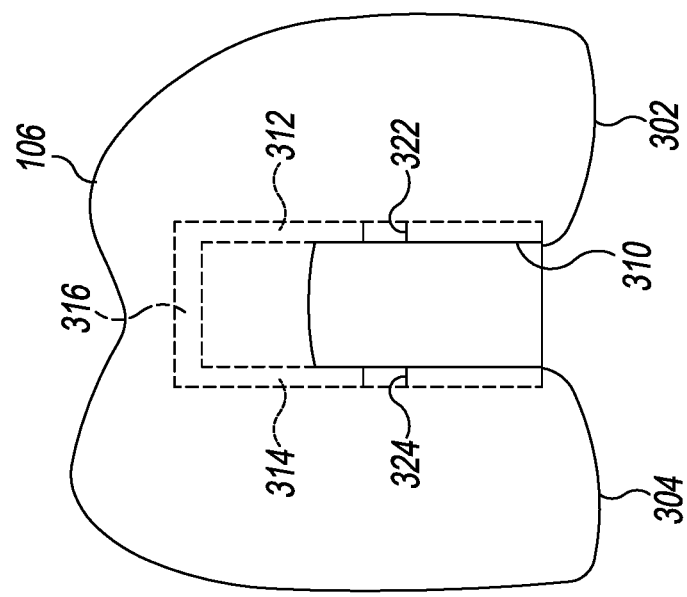
FIG. 3 is an inferior elevation view of an embodiment of the femoral component of the orthopaedic knee prosthesis of FIG. 1.

The illustrative femoral component 106 is configured to be coupled to a surgically-prepared surface of the distal end of a femur of the patient. As best shown in FIG. 3, the femoral component 106 includes a medial femoral condyle 302 configured to articulate on the medial articular surface 202 of the tibial insert 200 and a lateral femoral condyle 304 configured to articulate on the lateral articular surface 204. As discussed in more detail below in regard to FIG. 8, one or both of the femoral condyles 302, 304 may include a femoral articular surface that is defined by a constant radius of curvature.

The femoral condyles 302, 304 are spaced apart from each other, and the femoral component 106 includes an intercondylar compartment 310 defined between the femoral condyles 302, 304. The intercondylar compartment 310 includes a medial side wall 312, a lateral side wall 314, and an anterior wall 316. The intercondylar compartment 310 is sized and shaped to receive a portion of the hinge component 108. To facilitate connection of the hinge component 108 to the femoral component 106, the medial side wall 312 includes a medial aperture 322 and the lateral side wall 314 includes a lateral aperture 324. Each of the apertures 322, 324 are sized and positioned to receive a portion of the hinge component 108 as discussed in more detail below.

Referring back to FIG. 1, the hinge component 108 includes an elongated shaft 120, a medial hinge arm 122 that extends superiorly from a superior end 126 of the elongated shaft 120, and a lateral hinge arm 124 that also extends superiorly from the superior end 126 of the elongated shaft 120. The medial hinge arm 122 includes a medial axle 132 that extends medially away from the medial hinge arm 122. Similarly, the lateral hinge arm 124 includes a lateral axle 134 that extends laterally away from the lateral hinge arm 124.

In the illustrative embodiment, the hinge arms 122, 124 exhibit some amount of flexibility and can be moved toward each to allow the hinge component 108 to be connected to the femoral component 106. For example, an orthopaedic surgeon can apply an amount of force in the direction marked with arrows 150 to move the hinge arms 122, 124 toward each other, which reduces the diameter of the hinge component 108 and allows the hinge arms 122, 124 to be inserted into the intercondylar compartment 310. As such, it should be appreciated that the orthopaedic knee prosthesis 100 may be assembled in situ with the tibial tray 102 and tibial insert 104 implanted in the patient's tibia and the femoral component 106 implanted into the patient's femur. To do so, the orthopaedic surgeon may slide the elongated shaft 120 of the hinge component 108 through the aperture 212 of the tibial insert 104 and into the longitudinal internal passageway 118 of the tibial tray 102. Additionally, the orthopaedic surgeon may squeeze the hinge arms 122, 124 toward each other by apply pressure in the direction of arrows 150 to allow the hinge arms 122, 124 to be inserted into the intercondylar compartment 310. In this way, unlike traditional hinged knee prostheses, the orthopaedic knee prosthesis 100 may be assembled intraoperatively without the requirement of the removal of additional bone or tissue from the patient to facilitate the additional room that is usually required for the insertion of a typical hinged knee prosthesis, which is pre-assembled.

As shown in FIGS. 4-8, when the orthopaedic knee prosthesis 100 is assembled, the elongated shaft 120 of the hinge component 108 is located in the longitudinal internal passageway 118 of the tibial tray 102 and the hinge arms 122, 124 are located in the intercondylar compartment 310 such that the axles 132, 134 of the hinge arms 122, 124 are received in the apertures 322, 324 of the intercondylar compartment 310. That is, the hinge component 108 and the femoral component 106 are connected together via cooperation of the axles 132, 134 and the apertures 322, 324. For example, as best shown in FIG. 6, the medial axle 132 of the hinge arm 122 is received in the medial aperture 322 of the medial side wall 312 of the intercondylar compartment 310 of the femoral component 106. Similarly, the lateral axle 134 is received in the lateral aperture 324 of the lateral side wall 314 of the intercondylar compartment 310.

In the illustrative embodiment of FIGS. 4-8, each of the medial axle 132 and the lateral axle 134 are cylindrical in shape. Additionally, the medial axle 132 and lateral axle 134 are coaxial with each other and define a rotational axis 604 about which the femoral component 106 may rotate. For example, a medial side of the assembled orthopaedic knee prosthesis 100 is shown in FIG. 7 with the medial axle 132 of the medial hinge arm 122 of the hinge component 108 received in the aperture 322 of the medial side wall 312 of the intercondylar compartment 310. In such an assembled configuration, the femoral component 106 may rotate about the rotational axis 604 defined by the coaxial axles 132, 134 in an anterior-posterior direction 700 to articular with the tibial insert 104. Additionally, the hinge component 108 may rotate in a medial-lateral direction 702 within the longitudinal internal passageway 118 of the stem 116 of the tibial tray 102. That is, the hinge component 108 may rotate about an axis defined by the stem 116 of the tibial tray 102.

Figure 8:
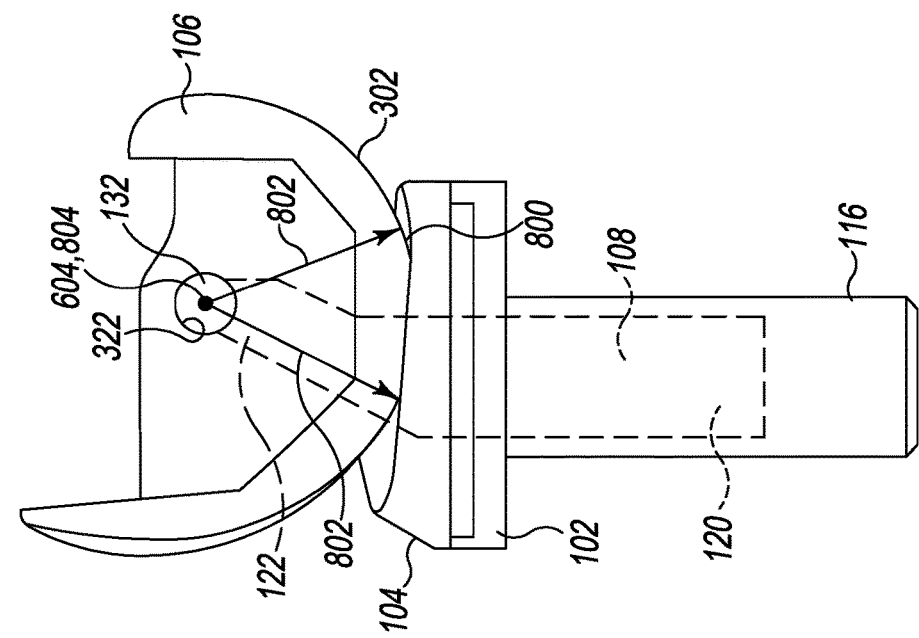
FIG. 8 is a medial elevation view of the orthopaedic knee prosthesis of FIG. 7 illustrating a center of a constant radius of curvature of a medial articular surface of the femoral component coaxial with an axis defined by a medial axle of the hinge component.

As discussed above, each of the medial femoral condyle 302 and the lateral femoral condyle 304 may include an articular surface that is defined by a constant radius of curvature. For example as shown in FIG. 8, the medial femoral condyle 302 includes an articular surface 800 that is defined by a constant radius of curvature 802. The arc length of the articular surface 800 may vary depending on the particular design and/or size of the femoral component 106. In the illustrative embodiment, for example, the constant radius of curvature 802 may extend anteriorly to a degree of hyperextension between 10 and 30 degrees (e.g., −20 degrees of flexion) and extend posteriorly to a degree of flexion between 30 and 70 degrees (e.g., 50 degrees). Of course, in other embodiments, the constant radius of curvature 802 may extend through a different range of extension and flexion. For example, the radius of curvature 802 may extend anteriorly to only around 0 degrees of flexion and/or extend posterior to a degree of flexion between 110 and 120 degrees. Additionally, in some embodiments, the constant radius of curvature 802 may be followed, posteriorly, by gradually decreasing radii of curvature that define the remainder of a sagittal shape of the femoral component 300. As such, the particular arc length of the constant radius of curvature 802 and the shape of the posterior articular surface 800 may be dependent on various design and implementation considerations.

In the illustrative embodiment, a center 804 of the constant radius of curvature 802 is coaxial with the rotational axis 604 defined by the medial axle 132 and the lateral axle 134. It should be appreciated that because the center 804 of the constant radius of curvature 802 is coaxial with the rotational axis 604, the femoral component 106 exhibits no significant anterior-posterior motion when rotating about the rotational axis 604 during extension-flexion of the orthopaedic knee prosthesis 100.

Figure 9:
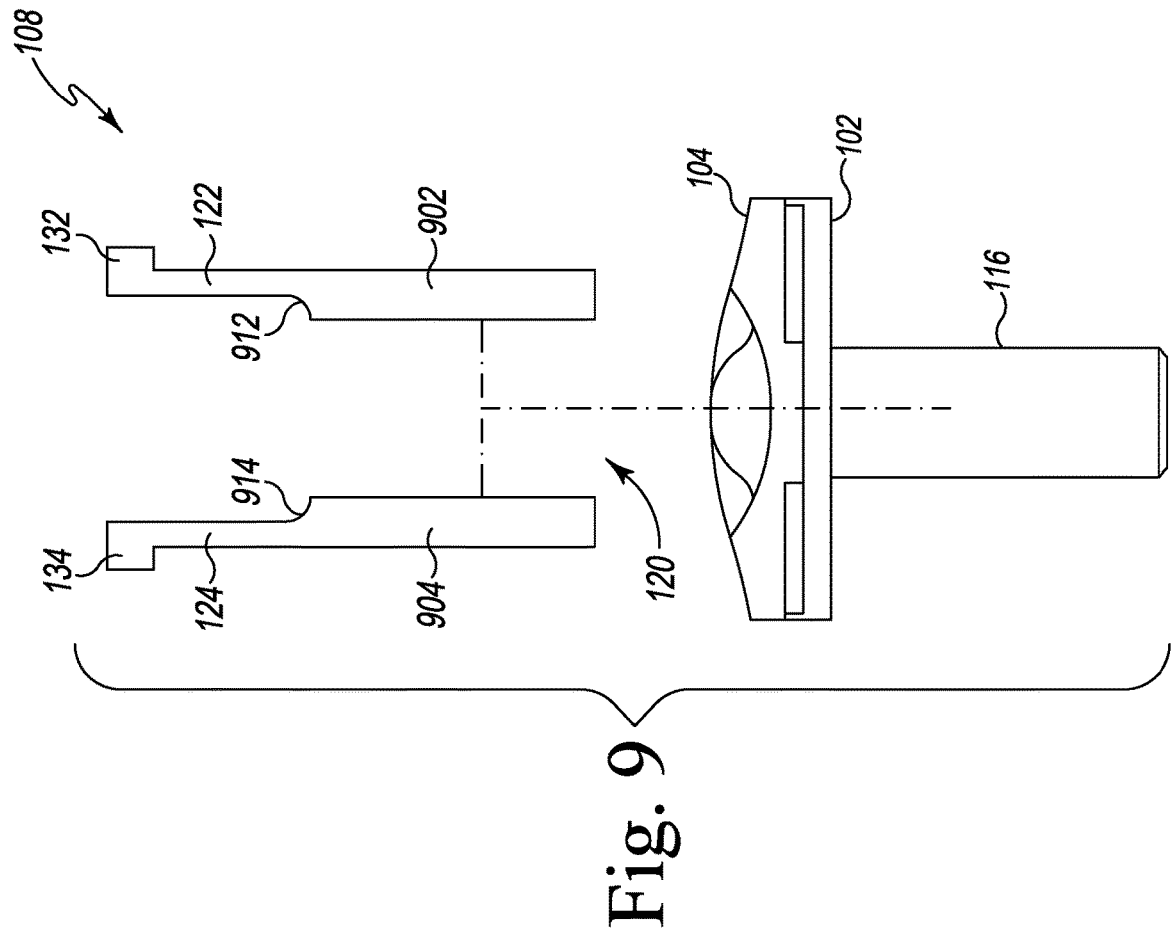
FIG. 9 is a partially-exploded view of the tibial insert and tibial tray of FIG. 1 and another embodiment of the hinge component that includes multiple elongated shaft components.

Referring now to FIG. 9, although the elongated shaft 120 of the hinge component 108 has been shown and described above as a unitary piece, it should be appreciated that the elongated shaft 120 may be modular and formed from multiple pieces in other embodiments. For example, the elongated shaft 120 may be embodied as a medial elongated shaft component 902 and a lateral elongated shaft component 904. In such embodiments, the medial hinge arm 122 extends from a superior end 912 of the medial elongated shaft component 902 and the lateral hinge arm 124 extends from a superior end 914 of the medial elongated shaft component 902. It should be appreciated that the modular construction of the elongated shaft 120 may allow for independent movement of the hinge arms 122, 124 to facilitate increased mobility of the orthopaedic knee prosthesis 100 in some embodiments as discussed in more detail below.

Figure 11:
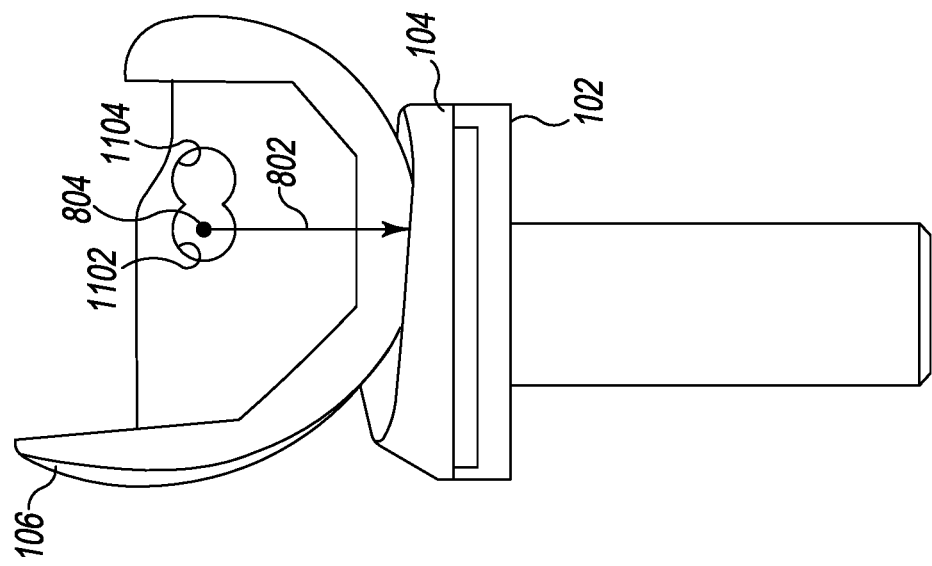
FIG. 11 is a medial elevation view of another embodiment of the orthopaedic knee prosthesis of FIG. 1 including a femoral component having multiple apertures spaced apart from each other and configured to receive an axle of the hinge component.
Figure 10:
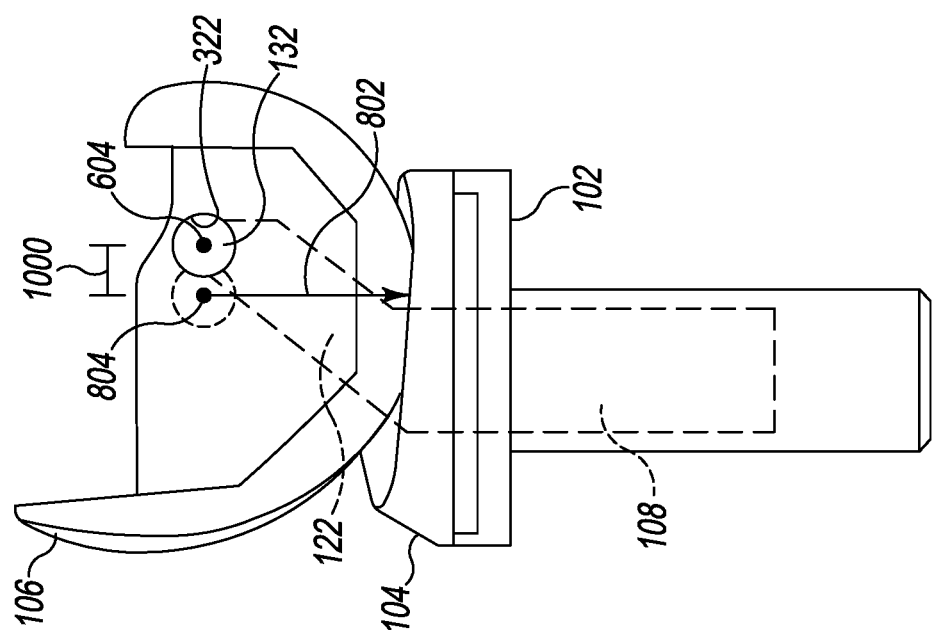
FIG. 10 is a medial elevation view of another embodiment of the orthopaedic knee prosthesis of FIG. 1 in an assembled configuration and showing an embodiment of a hinge component in phantom having a pair of axles that are offset from a center of a constant radius of curvature that defines an articular surface of the femoral component.

Referring now to FIG. 10, in some embodiments, the rotational axis 604 defined by the medial axle 132 and lateral axle 134 may be offset from the center 804 of the constant radius of curvature 802, which defines the articular surfaces of the femoral condyles 302, 304 as described above. For example, the rotational axis 604 may be offset posteriorly relative to the center 804 of the constant radius of curvature 802 by a distance 1000 of five to seven millimeters. To provide some selection in the amount of offset between the rotational axis 604 and the center 804 of the constant radius of curvature 802, the intercondylar compartment 310 of the femoral component 106 may include multiple apertures spaced apart from each other and each configured to receive one of the axles 132, 134. For example, as shown in FIG. 11, the medial side wall 312 of the intercondylar compartment 310 of the femoral component 106 may include an aperture 1102 that is coaxial with the center 804 of the constant radius of curvature 802 and one or more additional apertures 1104 that are offset from the center 804. In which way, the orthopaedic knee prosthesis 100 may be assembled in one of a number of configurations with each having a different offset and, as such, a different amount of anterior-posterior translation during flexion as discussed in more detail below. In the illustrative embodiment, each of the apertures 1102, 1104 are opened to each other, but each of the apertures 1100, 1102 may be closed in other embodiments.

Figure 13:
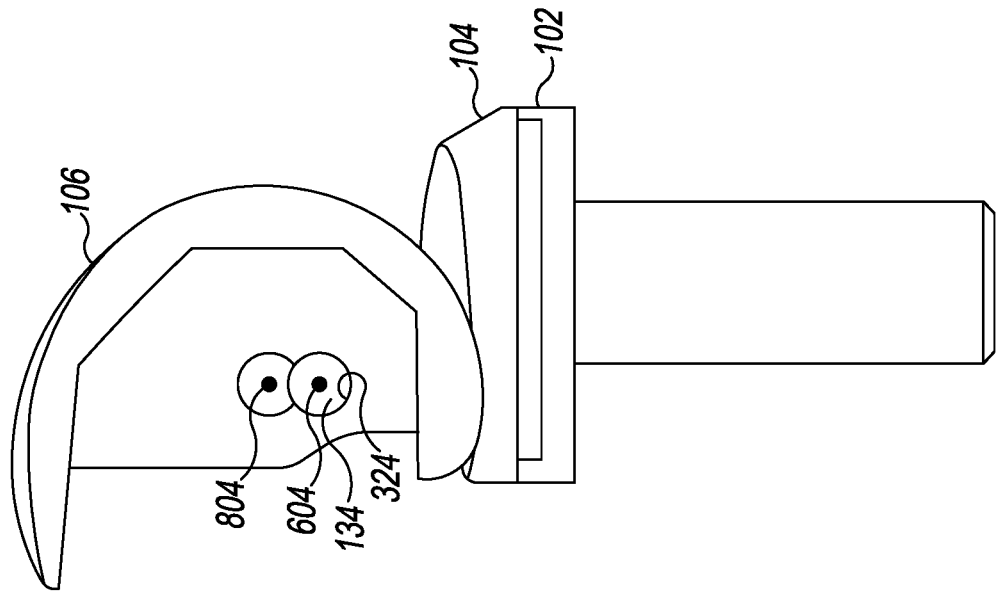
FIG. 13 is a lateral elevation view of the orthopaedic knee prosthesis of FIG. 11 shown in flexion and illustrating a posterior movement of the femoral component of the orthopaedic knee prosthesis during flexion.
Figure 12:
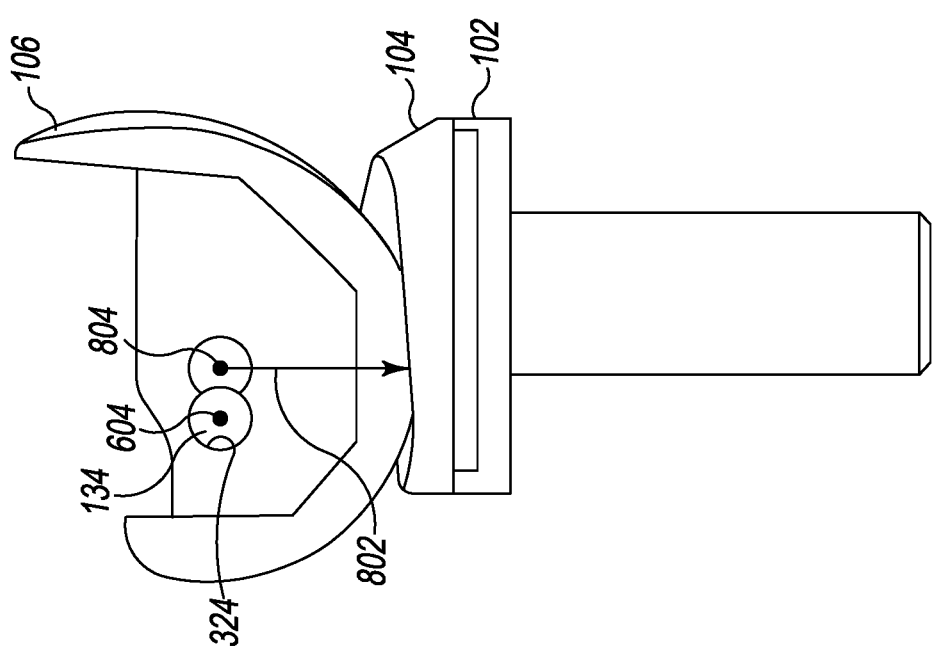
FIG. 12 is a lateral elevation view of the orthopaedic knee prosthesis of FIG. 11 shown in extension.

It should be appreciated that because the rotational axis 604 is posteriorly offset from the center 804 of the constant radius of curvature 802 that defines the articular surface of the femoral condyles 302, 304, the femoral component 106 will exhibit some amount of posterior movement during flexion. For example, the orthopaedic knee prosthesis 100 with an offset rotational axis 604 is shown in FIG. 12 in extension. As shown in FIG. 13, when the orthopaedic knee prosthesis 100 is flexed, the femoral component 106 rotates about the rotational axis 604 and also moves posteriorly, relative to its extension position of FIG. 12, due to the posterior offset between the rotational axis 604 and the center 804 of the constant radius of curvature 802. Illustratively, the rotational axis 604 is offset from the center 804 of the constant radius of curvature 802 by five to seven millimeters, which causes a corresponding five to seven millimeters of posterior movement of the femoral component 106 during flexion.

Figure 15:
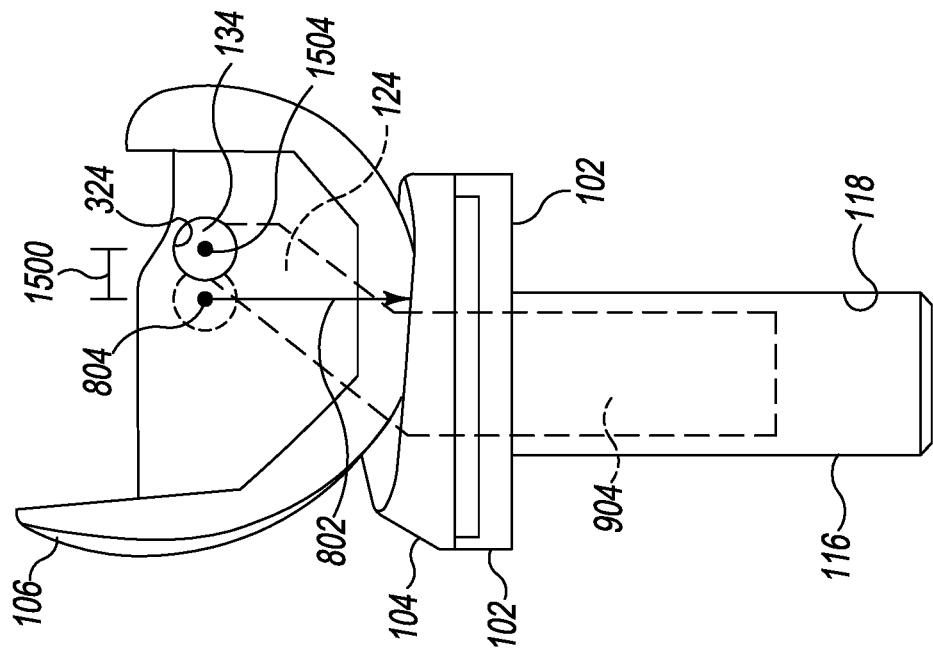
FIG. 15 is a lateral elevation view of the orthopaedic knee prosthesis of FIG. 14 and showing the hinge component in phantom including a lateral hinge arm having a lateral axle that is offset from a center of a constant radius of curvature that defines a lateral articular surface of the femoral component.
Figure 14:
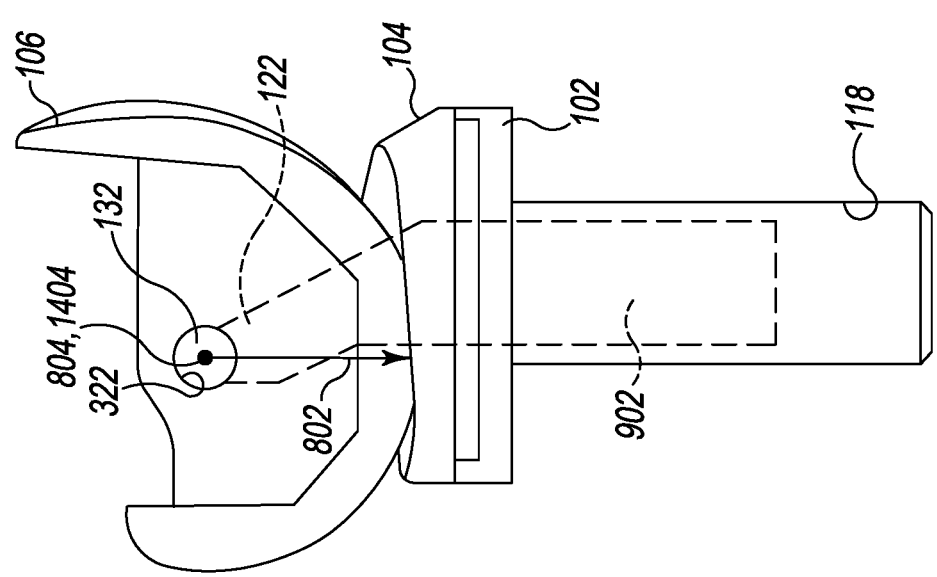
FIG. 14 is a medial elevation view of another embodiment of the orthopaedic knee prosthesis of FIG. 1 in an assembled configuration and showing an embodiment of a hinge component in phantom including a medial hinge arm having a medial axle that is coaxial with a center of a constant radius of curvature that defines a medial articular of the femoral component.

Referring now to FIGS. 14 and 15, in some embodiments, the medial axle 132 and the lateral axle 134 of the hinge component 108 may be non-coaxial with each other to provide an amount of asymmetric posterior movement to the femoral condyles 302, 304. In such embodiments, the elongated shaft 120 may be modular and formed from the medial elongated shaft component 902 and the lateral elongated shaft component 904 as discussed above in regard to FIG. 9.

Figure 16:
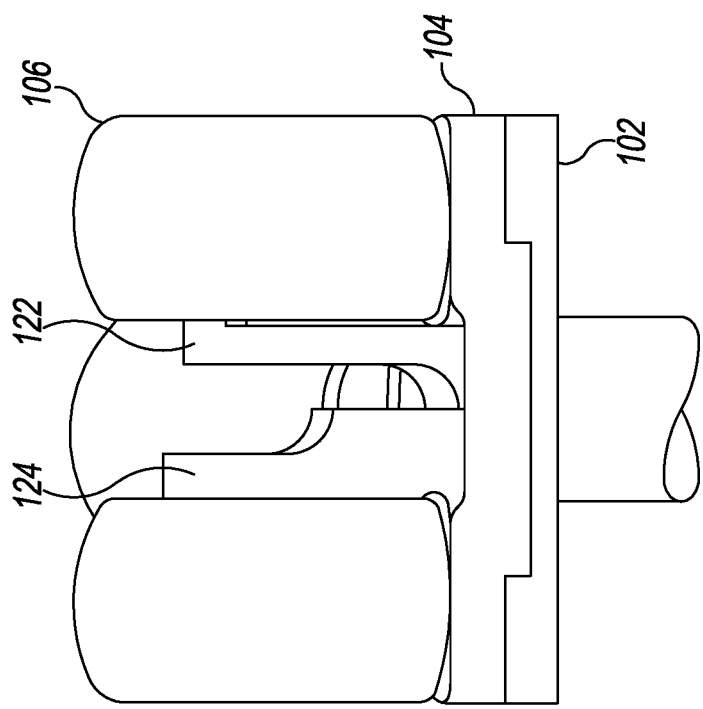
FIG. 16 is a posterior elevation view of the orthopaedic knee prosthesis of FIGS. 14 and 15 shown in hyperextension.

In the illustrative embodiment, as shown in FIG. 14, the medial axle 132 of the hinge component 108 defines a rotational axis 1404, which is coaxial with the center 804 of the constant radius of curvature 802. Conversely, as shown in FIG. 16, the lateral axle 134 of the hinge component 108 defines a rotational axis 1504 that is offset from the center 804 of the constant radius of curvature 802 by a distance 1500 (e.g., five to seven millimeters). The non-coaxial arrangement of the medial and lateral axles 132, 134 causes differential posterior movement between the medial femoral condyle 302 and the lateral femoral condyle 304 of the femoral component 106 during flexion. That is, the medial femoral condyle 302 exhibits a minimal amount of posterior movement during flexion. Conversely, the lateral femoral condyle 304 exhibits a larger amount of posterior movement during flexion due to the offset distance 1500, which causes a medial pivot of the femoral component 106 relative to the tibial insert 104. In some embodiments, the lateral aperture 324 may be elongated or otherwise embodied as a slot to better allow posterior movement of the lateral axle 134.

Figure 17:
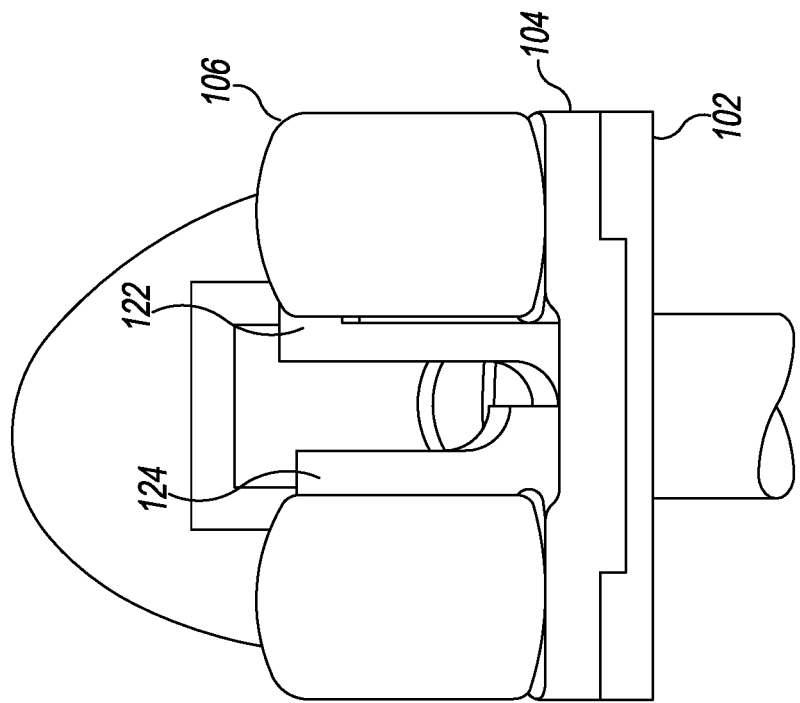
FIG. 17 is a posterior elevation view of the orthopaedic knee prosthesis of FIGS. 14 and 15 shown in extension.
Figure 19:
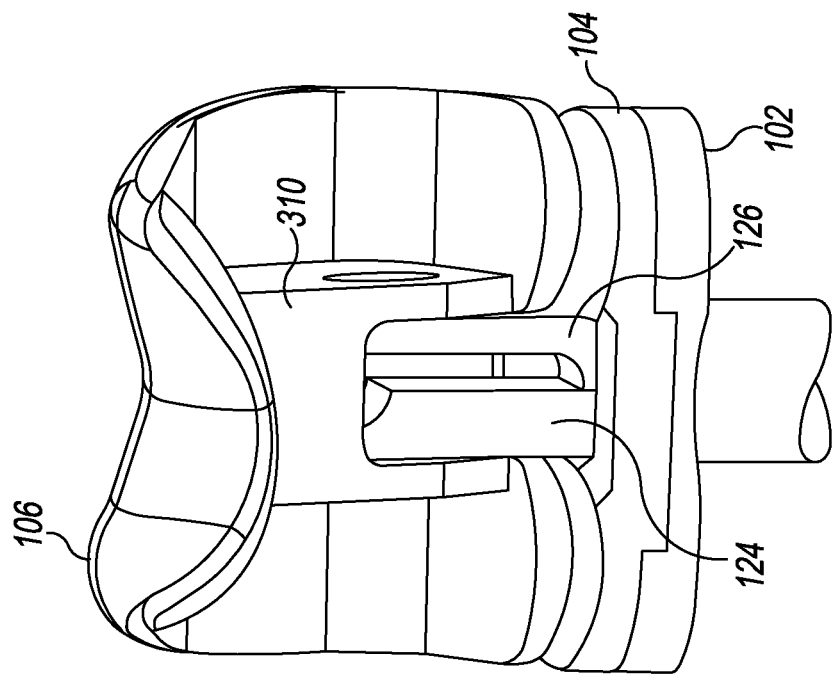
FIG. 19 is a posterior elevation view of the orthopaedic knee prosthesis of FIGS. 14 and 15 shown in flexion.
Figure 18:
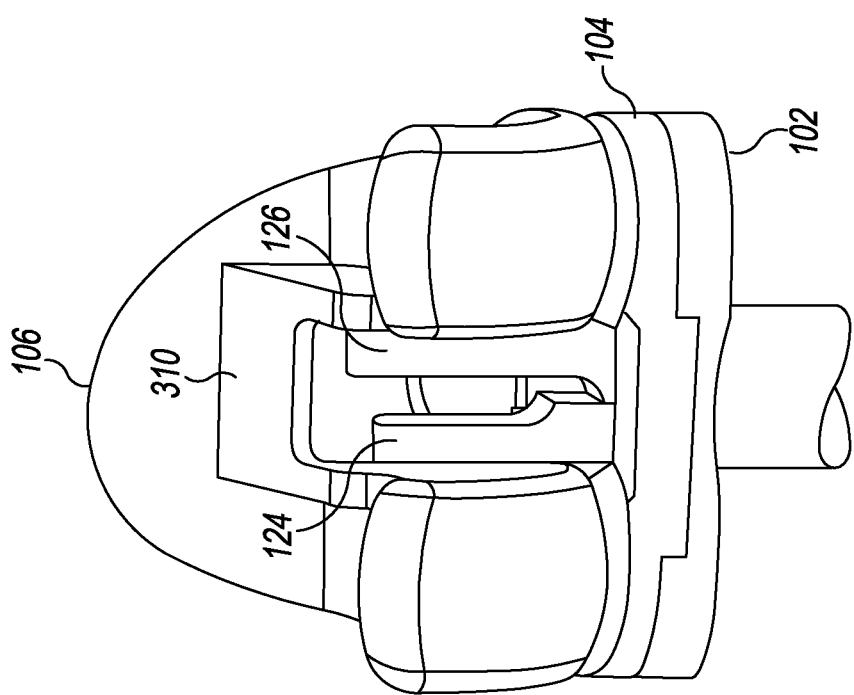
FIG. 18 is a posterior elevation view of the orthopaedic knee prosthesis of FIGS. 14 and 15 shown in mid-flexion.

As discussed above, the embodiment of the orthopaedic knee prosthesis 100 of FIGS. 14 and 15 may include a modular elongated shaft 120 embodied as the medial elongated shaft component 902 and the lateral elongated shaft component 904 to facilitate independent movement of the hinge arms 122, 124. For example, in FIG. 16-19, the orthopaedic knee prosthesis 100 of FIGS. 14 and 15 is shown in different degrees of flexion. In FIG. 16, the orthopaedic knee prosthesis 100 is shown in hyperextension. In such a position, the lateral hinge arm 124 is raised relative to the medial hinge arm 122. In FIG. 17, the orthopaedic knee prosthesis 100 is shown in extension, at which the lateral hinge arm 124 is raised relative to the medial hinge arm 122. In FIG. 18, the orthopaedic knee prosthesis 100 is shown in mid-flexion, and the lateral hinge arm 124 is raised further superior to the medial hinge arm 122. In FIG. 19, the orthopaedic knee prosthesis 100 is shown in deep flexion, and the lateral hinge arm 124 is raised even further superior to the medial hinge arm 122. As discussed above, the lateral femoral condyle 304 of the femoral component 106 also moves posteriorly during flexion, resulting in medial pivoting of the femoral component 106 relative to the tibial insert 104.

Figure 20:
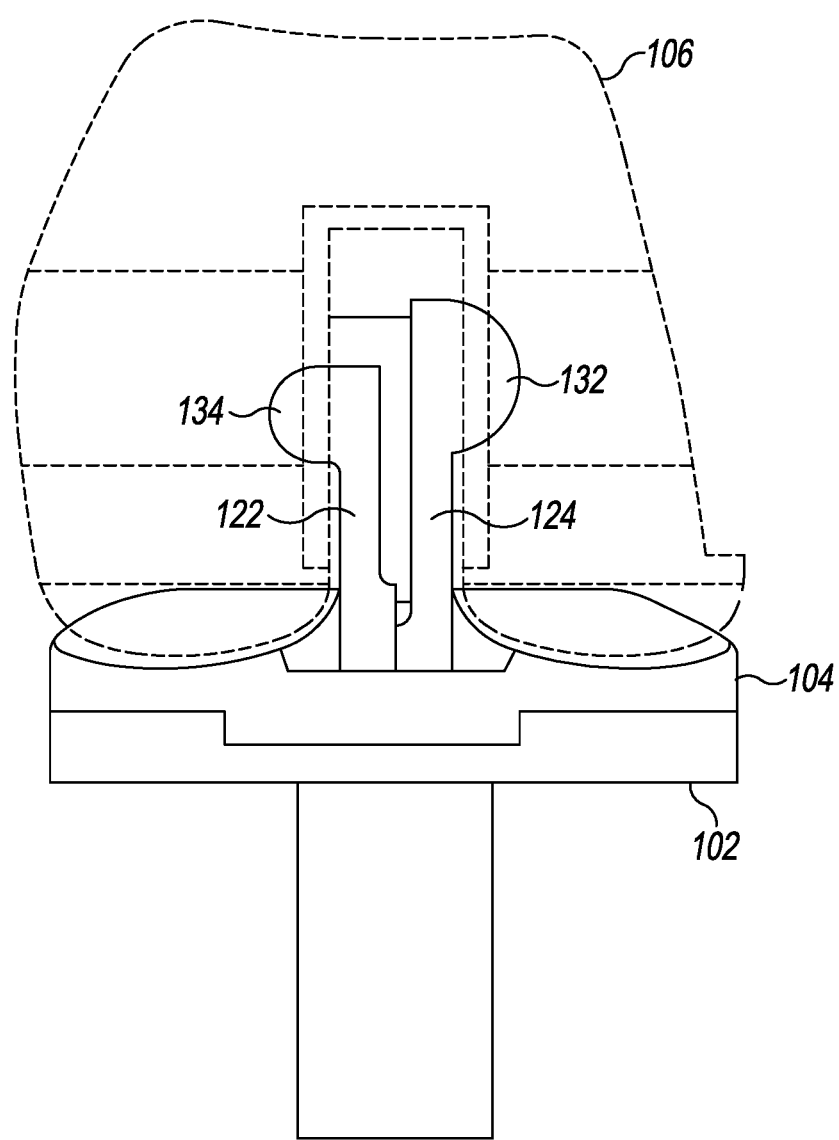
FIG. 20 is a posterior elevation view of another embodiment of the orthopaedic knee prosthesis of FIG. 1 in an assembled configuration showing the femoral component in phantom and including a hinge component having a medial axle and lateral axle of different sizes.
Figure 21:
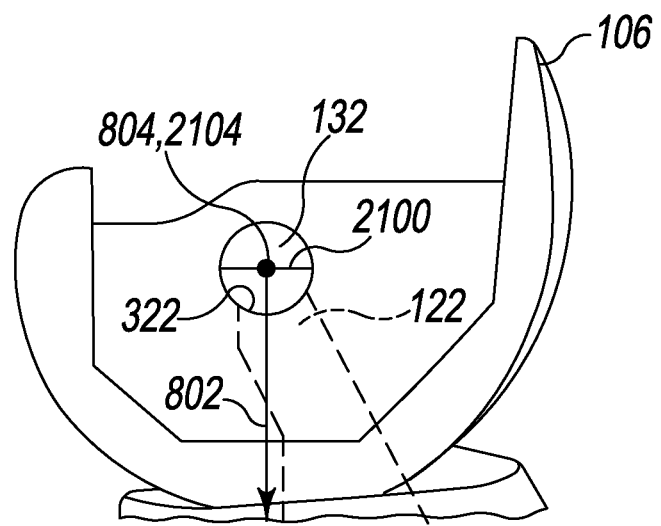
FIG. 21 is a medial elevation view of the femoral component of the orthopaedic knee prosthesis of FIG. 20 with the hinge component partially shown in phantom and having the medial axle received in a medial aperture of the femoral component that is coaxial with a center of a constant radius of curvature that defines a medial articular surface of the femoral component.
Figure 22:
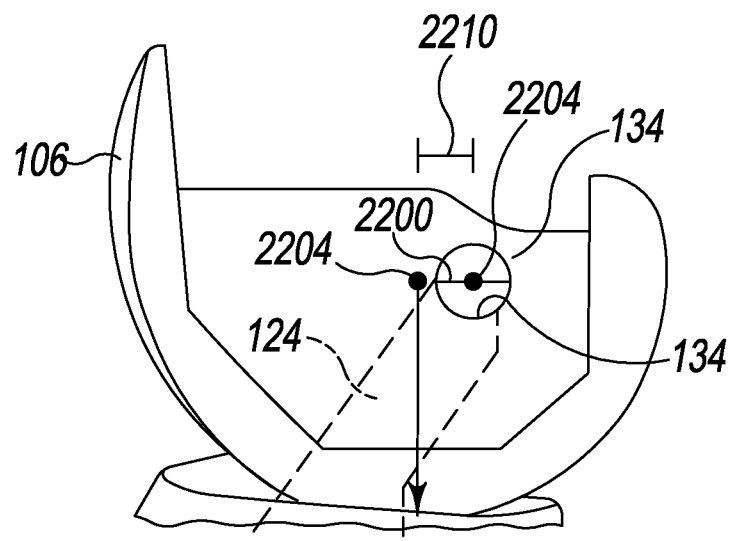
FIG. 22 is a lateral elevation view of the femoral component of the orthopaedic knee prosthesis of FIG. 20 with the hinge component partially shown in phantom and having the lateral axle received in a lateral aperture of the femoral component that is offset from a center of a constant radius of curvature that defines a lateral articular surface of the femoral component.

Referring now to FIGS. 20-24, in some embodiments, the shape and size of the medial axle 132 and the lateral axle 134 may be different to further facilitate the differential movement of the medial and lateral condyles 302, 304 of the femoral component 106 during flexion. For example, as shown in FIG. 20, each of the medial axle 132 and the lateral axle 134 may include a hemispherical outer surface. However, the diameter for the each hemispherical outer surface is different. For example, as shown in FIG. 21, the medial axle 132 has a hemispherical outer surface having a diameter 2100. The medial axle 132 also a rotational axis 2104 that is coaxial with the center 804 of the constant radius of curvature 802 that defines the articular surface of the medial femoral condyle 302 of the femoral component 106. As shown in FIG. 22, the lateral axle 134 also has a hemispherical outer surface, but the hemispherical outer surface of the lateral axle 134 has a diameter 2200 that is larger than the diameter 2100 of the hemispherical outer surface of the medial axle 132. Additionally, the lateral axle 134 defines a rotational axis 2204 that is offset from the center 804 of the constant radius of curvature 802 by a distance 2210. Depending on the desired amount of posterior movement of the lateral femoral condyle 304, the distance 2210 may be five to seven millimeters, for example.

Figure 24:
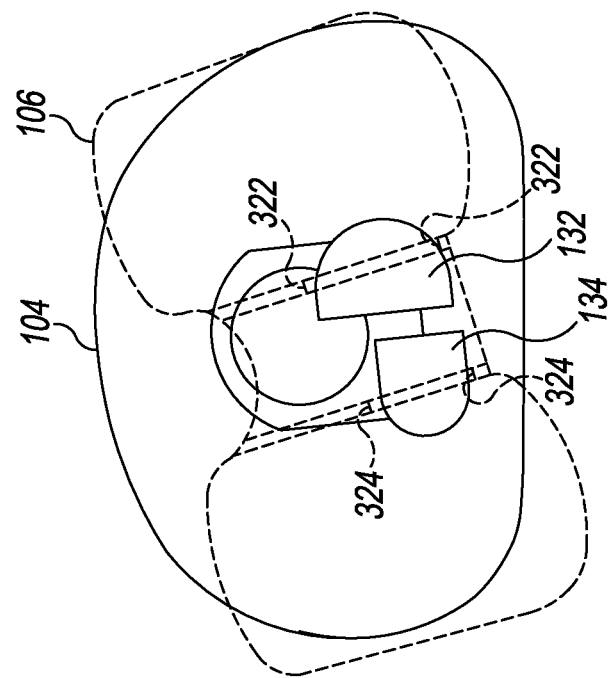
FIG. 24 is a top plan view of the orthopaedic knee prosthesis of FIG. 1 with the femoral component shown in phantom pivoted medially.
Figure 23:
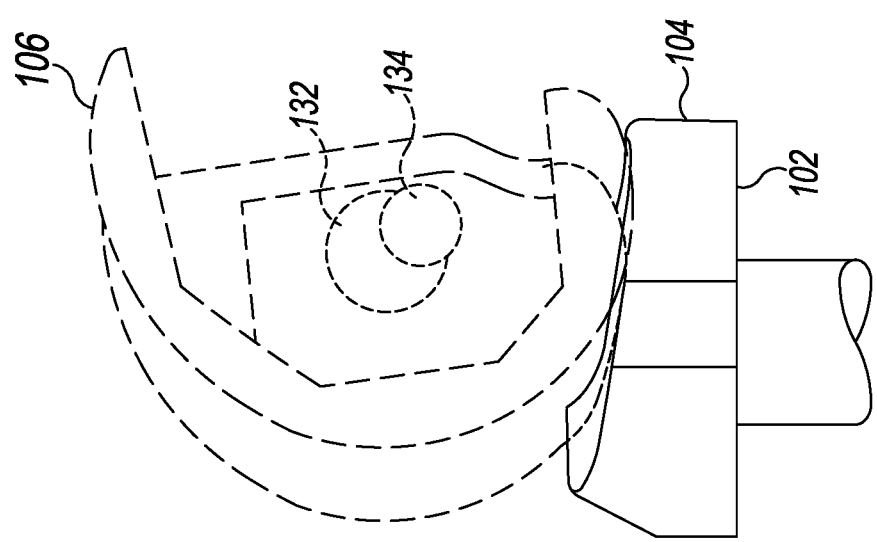
FIG. 23 is a lateral perspective view of the orthopaedic knee prosthesis of FIG. 20 with the femoral component shown in phantom in flexion.

As shown in FIGS. 23 and 24, as the orthopaedic knee prosthesis 100 of FIGS. 20-22 is moved through flexion, the femoral component 106 exhibits an amount of internal rotation. That is, in addition to any rotation of the hinge component 108 itself, as discussed above, the medial aperture 322 of the intercondylar compartment 310 of the femoral component 106 may move across the hemispherical outer surface of the medial axle 132. Similarly, the lateral aperture 324 of the intercondylar compartment 310 of the femoral component 106 may move across the hemispherical outer surface of the lateral axle 134. For example, the medial aperture 322 may move anteriorly on the hemispherical outer surface of the medial axle 132, while the lateral aperture 324 may move posteriorly on the hemispherical outer surface of the lateral axle 134.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic prosthesis comprising:
   a tibial tray having a platform configured to be coupled to a surgically-prepared surface of the proximal end of a tibia and a stem extending inferiorly from a bottom surface of the platform, wherein the stem includes a longitudinal internal passageway;
   a tibial insert configured to be coupled to the platform, wherein the tibial insert includes a pair of articular surfaces and an aperture defined between the pair of articular surfaces;
   a hinge component comprising (i) an elongated shaft configured to be received through the aperture of the tibial insert and into the longitudinal internal passageway of the tibial tray, (ii) a medial hinge arm extending superiorly from a superior end of the elongated shaft and having a medial axle extending medially therefrom, and (iii) a lateral hinge arm extending superiorly from the superior end of the elongated shaft and having a lateral axle extending laterally therefrom;
   a femoral component configured to be coupled to a surgically-prepared surface of the distal end of a femur, the femoral component having (i) a pair of spaced apart condyles configured to articulate on the articular surfaces of the tibial insert and (ii) an intercondylar compartment defined between the pair of spaced apart condyles, wherein the intercondylar compartment includes a medial side wall having an aperture defined therein and a lateral side wall having an aperture defined therein,
   wherein the medial axle of the medial hinge arm is configured to be received in the aperture of the medial side wall of the intercondylar compartment and the lateral axle of the lateral hinge arm is configured to be received in the aperture of the lateral side wall of the intercondylar compartment.

2. The orthopaedic prosthesis of claim 1, wherein the pair of hinge arms are moveable toward each other to allow insertion of the pair of hinge arms into the intercondylar compartment of the femoral component.

3. The orthopaedic prosthesis of claim 1, wherein each of the medial axle and the lateral axle is cylindrical.

4. The orthopaedic prosthesis of claim 1, wherein the medial axle and the lateral axle are coaxial with each other and cooperate to define a rotation axis about which the femoral component is configured to rotate in an anterior-posterior direction during articulation on the articular surfaces of the tibial insert.

5. The orthopaedic prosthesis of claim 4, wherein the tibial insert is configured to rotate on the platform in a medial-lateral direction about an axis defined by the stem of the platform.

6. The orthopaedic prosthesis of claim 4, wherein the pair of spaced apart condyles of the femoral component includes a medial condyle having a medial articular surface defined by a first constant radius of curvature and a lateral condyle having a lateral articular surface defined by a second constant radius of curvature, and wherein the rotation axis defined by the medial axle and the lateral axle is coaxial with the center of the first constant radius of curvature and with the center of the second constant radius of curvature.

7. The orthopaedic prosthesis of claim 4, wherein the pair of spaced apart condyles of the femoral component includes a medial condyle having a medial articular surface defined by a first constant radius of curvature and a lateral condyle having a lateral articular surface defined by a second constant radius of curvature, wherein a center of the first constant radius of curvature is coaxial with a center of the second constant radius of curvature to define a curvature axis, and wherein the rotation axis defined by the medial axle and the lateral axle is posteriorly offset from the curvature axis to cause posterior movement of the femoral component, relative to the tibial insert, during flexion of the orthopaedic prosthesis.

8. The orthopaedic prosthesis of claim 7, wherein the rotation axis defined by the medial axle and the lateral axle is posteriorly offset from the curvature axis by a distance of five to seven millimeters.

9. The orthopaedic prosthesis of claim 7, wherein the medial side wall of the intercondylar compartment includes (i) a first aperture configured to receive the medial axle of the medial hinge arm and (ii) a second aperture configured to receive the medial axle and posteriorly offset from the first aperture, and wherein the lateral side wall of the intercondylar compartment includes (i) a first aperture configured to receive the lateral axle of the lateral hinge arm and located coaxially with the first aperture of the medial side wall and (ii) a second aperture configured to receive the lateral axle and located coaxially with the second aperture of the medial side wall.

10. The orthopaedic prosthesis of claim 1, wherein the medial axle and the lateral axle are non-coaxial with each other.

11. The orthopaedic prosthesis of claim 10, wherein the elongated shaft of the hinge component includes a medial elongated shaft component and a lateral elongated shaft component separate from the medial elongated shaft component, wherein the medial hinge arm extends superiorly from a superior end of the medial shaft component and the lateral hinge arm extends superiorly from the lateral shaft component, and wherein the medial axle defines a first axis and the lateral axle defines a second axis that is non-coaxial with the first axis.

12. The orthopaedic prosthesis of claim 11, wherein the pair of spaced apart condyles of the femoral component includes a medial condyle having a medial articular surface defined by a first constant radius of curvature and a lateral condyle having a lateral articular surface defined by a second constant radius of curvature, wherein the first axis defined by the medial axle is coaxial with a center of the first constant radius of curvature, and wherein the second axis defined by the lateral axle is posteriorly offset from a center of the second constant radius of curvature to cause posterior movement of the lateral condyle of the femoral component, relative to the medial condyle, during flexion of the orthopaedic prosthesis.

13. The orthopaedic prosthesis of claim 12, wherein the second axis defined by the lateral axle is posteriorly offset from the center of the second constant radius of curvature by five to seven millimeters.

14. The orthopaedic prosthesis of claim 12, wherein the medial axle has a hemispherical outer surface and the lateral axle has a hemispherical outer surface having a diameter that is less than a diameter of the hemispherical outer surface of the medial axle, and wherein the aperture of the lateral side wall of the intercondylar compartment of the femoral component has a diameter less than a diameter of the aperture of the medial side wall of the intercondylar compartment.

15. The orthopaedic prosthesis of claim 14, wherein the aperture of the medial wall is configured to move posteriorly on the hemispherical outer surface of the medial axle and the aperture of the lateral wall is configured to move anteriorly on the hemispherical outer surface of the lateral axle during flexion of the orthopaedic prosthesis.

16. An orthopaedic prosthesis comprising:

a tibial tray having a platform configured to be coupled to a surgically-prepared surface of the proximal end of a tibia and a stem extending inferiorly from a bottom surface of the platform, wherein the stem includes a longitudinal internal passageway;

a tibial insert configured to be coupled to the platform, wherein the tibial insert includes a medial articular surface, a lateral articular surface, and an aperture defined between the medial articular surface and the lateral articular surface;

a hinge component including an elongated shaft configured to be received through the aperture of the tibial insert and into the longitudinal internal passageway of the tibial tray, wherein the elongated shaft includes (i) a medial elongated shaft component and a lateral elongated shaft component separate from the medial elongated shaft component, (ii) a medial hinge arm extending superiorly from a superior end of the medial elongated shaft component and having a medial axle extending medially therefrom, wherein the medial axle has a hemispherical outer surface, and (iii) a lateral hinge arm extending superiorly from a superior end of the lateral elongated shaft component and having a lateral axle extending laterally therefrom, wherein the lateral axle has a hemispherical outer surface having a diameter that is less than a diameter of the hemispherical outer surface of the medial axle and wherein the medial axle and the lateral axle are non-coaxial; and a femoral component configured to be coupled to a surgically-prepared surface of the distal end of a femur, the femoral component having (i) a medial condyle configured to articulate on the medial articular surface of the tibial insert, (ii) a lateral condyle configured to articulate on the lateral articular surface of the tibial insert, and (iii) an intercondylar compartment defined between the pair of spaced apart condyles, wherein the intercondylar compartment includes a medial side wall having an aperture defined therein and a lateral side wall having an aperture defined therein that has a diameter less than a diameter of the aperture defined in the medial side wall, wherein the medial axle is configured to be received in the aperture of the medial side wall and the lateral axle is configured to be received in the aperture of the lateral side wall.

17. The orthopaedic prosthesis of claim 16, wherein the medial condyle of the femoral component includes a medial articular surface defined by a first constant radius of curvature and the lateral condyle includes a lateral articular surface defined by a second constant radius of curvature,
wherein a first axis defined by the medial axle is coaxial with a center of the first constant radius of curvature, and
wherein a second axis defined by the lateral axle is posteriorly offset from a center of the second constant radius of curvature to cause posterior movement of the lateral condyle of the femoral component, relative to the medial condyle, during flexion of the orthopaedic prosthesis.

18. A hinge component for a hinged orthopaedic prosthesis, the hinge component comprising:
an elongated shaft configured to be received into an internal passageway of a tibial tray;
a medial hinge arm extending superiorly from the elongated shaft and including a medial axle extending medially therefrom; and
a lateral hinge arm extending superiorly from the elongated shaft and including a lateral axle extending laterally therefrom, wherein the medial axle defines a first axis and the lateral axle defines a second axis that is non-coaxial with the first axis,
wherein the medial hinge arm and the lateral hinge arm are movable toward each other to allow insertion of the medial and lateral arms into an intercondylar compartment of a femoral.

19. The hinge component of claim 18, wherein the elongated shaft includes a medial elongated shaft component and a lateral elongated shaft component separate from the medial elongated shaft component,
wherein the medial hinge arm extends superiorly from a superior end of the medial shaft component and the lateral hinge arm extends superiorly from the lateral shaft component.

* * * * *